(12) United States Patent
Kim et al.

(10) Patent No.: US 7,083,969 B2
(45) Date of Patent: Aug. 1, 2006

(54) *SERRATIA MARCESCENS* STRAIN

(75) Inventors: Hwanmook Kim, Yusong-Ku (KR);
Youngkook Kim, Taejon (KR);
Sangbae Han, Choongcheongbuk-do (KR); Sungrak Yoo, Seoul (KR)

(73) Assignee: Korea Research Institute of Bioscience and Biotechnology, Daejon (KR)

( * ) Notice: Subject to any disclaimer, the term of this patent is extended or adjusted under 35 U.S.C. 154(b) by 486 days.

(21) Appl. No.: 10/662,723

(22) Filed: Sep. 15, 2003

(65) Prior Publication Data

US 2005/0069560 A1    Mar. 31, 2005

Related U.S. Application Data

(62) Division of application No. 09/509,118, filed as application No. PCT/KR98/00287 on Sep. 19, 1998, now Pat. No. 6,645,962.

(30) Foreign Application Priority Data

Sep. 20, 1997    (KR) .................................. 97-47869

(51) Int. Cl.
*C12N 1/20* (2006.01)
*C12P 17/16* (2006.01)

(52) U.S. Cl. .................................... 435/252.1; 435/118

(58) Field of Classification Search ...................... None
See application file for complete search history.

(56) References Cited

U.S. PATENT DOCUMENTS 4,266,028 A    5/1981   Nakamura et al.

OTHER PUBLICATIONS

Domingo Gargallo-Viola, Enzyme Polymorphism, Prodigiosin Production, and Plasmid Fingerprints in Clinical and Naturally Occurring Isolates of *Serratia marcescens*, Journal of Clinical Microbiology, May 1989, pp. 860-868.
N.R. Thomson, et al., Biosynthesis of carbapenem antibiotic and prodigiosin pigment in *Serratia* is under quorum sensing control, Molecular Microbiology (2000) 36(3), pp. 539-556.
Sang Bae Han, et al., T-cell specific immunosuppression by prodigiosin isolated from *Serratia marcescens*, International Journal of Immunopharmacology 20 (1998), pp. 1-13.

*Primary Examiner*—Irene Marx
(74) *Attorney, Agent, or Firm*—Mathews, Sheperd, McKay & Bruneau, P.A.

(57) ABSTRACT

There are disclosed a novel microorganism *Serratia marcescens* strain and a prodigiosin isolated from the microorganism. The prodigiosin is useful as an immunosuppressive in various fields, including the treatment of the diseases requiring immunosuppression and the basic research for the diseases, the transplantation of the organs or tissues, and the immune cells.

1 Claim, No Drawings

SERRATIA MARCESCENS STRAIN

This application is a divisional application of U.S. Ser. No. 09/509,118, which was filed on Jun. 7, 2000 now U.S. Pat. No. 6,645,962.

TECHNICAL FIELD

The present invention relates to a novel *Serratia marcescens* strain, a prodigiosin, and the use of the prodigiosin in immunosuppression fields. More particularly, the present invention relates to a novel *Serratia marcescens* strain which can produce the prodigiosin, and the use of the prodigiosin as an immunosuppressive.

BACKGROUND ART

Over the recent few years, active study and research have been and continued to be directed to the development of immunosuppressives, which are useful for the study on immunocytes and immune responses and for the treatment of the diseases requiring immunosuppression. For instance, immunosuppressives are utilized in researching almost all of immune responses, including cytokine production, T-cell activation, antibody production, cell death, DNA synthesis, immunocyte differentiation, intracellular signal transduction, etc. The immunosuppressives are also used to treat the diseases attributable to exaggerated immune responses, such as hypersensitive immune response and allergies. In addition, they are needed to suppress excess immune responses upon transplantation of organs, such as the kidney, the liver, the pancreas, marrow, the heart, skin, the lung, etc.

Prevailing immunosuppressives include, for example, cyclosporin A, cyclophosphamide, rapamycin, FK-506, etc. Many immunosuppressives which show similar or different suppressing behaviors are now under research.

The microorganisms belonging to genus *Streptomyces* or *Serratia* produce red substances of pyrrolylpyromethene structures, examples of which include prodigiosin, metacycloprodigiocin, prodigiosene, methoxyprodigiosin, and prodigiosin 25-C. They are now known to be of antibacterial and antimalarial activity and, particularly, prodigiosin 25-C shows an immunosuppressing effect.

DISCLOSURE OF THE INVENTION

It is an object of the present invention to provide a novel strain *Serratia marcescens* which produce a prodigiosin.

It is another object of the present invention to provide a prodigiosin as an immunosuppressive.

BEST MODES FOR CARRYING OUT THE INVENTION

The detailed description of the present invention will follow isolation of a desired microorganism strain; mycological characterization of the strain; extraction of prodigiosin with organic solvent; purification of prodigiosin through silica gel column and thin layer chromatography; structure analysis through nuclear magnetic resonance; utility of the prodigiosin as an immunosuppressive.

Germ-free test animals, mice BDF1 and B6C3F1, obtained from Genetic Resources Center, Korean Research Institute of Bioscience and Biotechnology in the Korean Institute of Science and Technology, were used for the assay of the immunosuppressive activity of prodigiosin. The data from the ex vivo experiments concerning the immunosuppressive effect of prodigiosin show that as much as 300 nM of prodigiosin has a cytotoxic effect, but no effects at less than 100 nM. At such concentrations as show no cytotoxic effects, prodigiosin cannot suppress the immune response of B lymphocytes. Prodigiosin had no influence on the antibody production and proliferation of B lymphocytes, but has a potential suppressive effect on the proliferation and activity of T lymphocytes. This selective immunosuppression for T lymphocytes is not ascribed to the selective cytotoxicity for T lymphocytes. The same immunosuppression results as in the ex vivo experiments were obtained in in vivo experiments. When T lymphocyte activity was measured by use of a graft versus host reaction and a T cell-dependent antibody producing reaction, the prodigiosin suppressed the immune response, but exerted no toxicity on animals. Therefore, the immunosuppressive activity of the prodigiosin is thought to be attributed to the selective suppression for T lymphocyte activity.

Prodigiosin 25-C, an immunosuppressive analogous to, but different from prodigiosin in structure and molecular weight, is known to suppress the proliferation of T lymphocytes, but not the proliferation of B lymphocytes. Of T lymphocytes, CD8 T lymphocytes are suppressed, but CD4 T lymphocytes are not. In contrast, the prodigiosin of the present invention has an immunosuppressive activity on CD8 T lymphocytes and CD4 T lymphocytes, both. This immunosuppressive activity is similar to those of other preexisting immunosuppressives. Like commercially available immunosuppressives, such as Cyclosporin A, Cyclophosphamide, FK-506 and Rapamycin, the prodigiosin of the invention selectively suppress the immune response of T lymphocytes.

The reaction systems used in the present invention are illustrative of the application of prodigiosin for a basic research of immunology, but not limitative of the use of prodigiosin. The immunosuppressives in current use are needed in various fields. First of all, the treatment of the diseases requiring immunosuppression and the basic research therefor require them. Immunosuppressive drugs are useful to remove the immune response which follows the transplantation of organs or tissues. Another application field of immunosuppressives is a basic research related to immune cells. In this field are included studies on cytokines, activation and differentiation of immune cells, and intracellular signal transduction. Cyclosporin A, Cyclophosphamide, FK-506 and Ripamycin are available for this field. Because the prodigiosin of the present invention has an activity similar to that of the above immunosuppressives, it can be used as a curing agent and a standard in such various fields.

The prodigiosin of the present invention was found to have the following chemical formula with a molecular weight of 323 as measured by NMR.

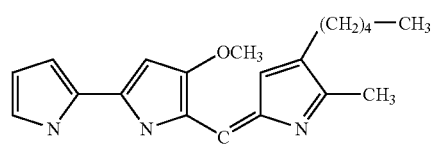

A better understanding of the present invention may be obtained in light of the following examples which are set forth to illustrate, but are not to be construed to limit the present invention.

EXAMPLE I

Culturing of a *Serratia marcescens* Strain and Isolation of Prodigiosin

Soil samples were taken from a silt area in Mokpo, Korea. A bacterial group belonging to *Serratia* spp. was isolated from the samples and named *Serratia marcescens* B-1231. It was deposited in Korean Collection for Type Cultures, Korean Research Institute of Bioscience and Biotechnology on Sep. 19, 1997 and received a Deposition No. KCTC-0386BP. In order to obtain an immunosuppressive, the *Serratia marcescens* B-1231 was cultured at 28° C. for 62 hours in a 1 L Erlenmeyer flask containing a basic medium which consisted of soluble starch 1%, phamamedia 0.5%, glucose 0.2%, ammonium sulfate 0.1%, potassium phosphate 0.1%, $MgSO_4.7H_2O$ 0.05%, calcium chloride 0.1% and NaCl 0.3%, at pH 7.0. An equal amount of ethyl acetate was added to the culture and they were sufficiently mixed for 30 min to give an organic layer. As the organic layer was concentrated under a reduced pressure, a red substance was obtained. This was separated by silica-gel column chromatography using as a mobile phase a mixture of chloroform and methanol. Following this, silica gel thin layer chromatography was carried out to purify the object material.

EXAMPLE II

In Vitro Experiment for Cytotoxicity Effect of Prodigiosin on Lymphocytes

Immune cells were separated from the spleens of the germ-free animals and cultured in vitro. The cultures were treated with the prodigiosin at various amounts from 3 nM to 30,000 nM and the viability of the cells were measured from the first day to the third day after the treatment. Based on the initial viability of the immune cells, the viabilities of the test groups were calculated. The results are given as shown in Table 1, below. As apparent from the data, the viability of the treated immune cells is significantly decreased at a concentration not less than 300 nM when being compared with that of an untreated control. So, subsequent experiments for immunoactivity were carried out at not more than 100 nM in order to exclude the cytotoxicity and to measure only the immunosuppressive effect of the prodigiosin.

TABLE 1

Effect of Prodigiosin on the Viability of Immune Cells

| Groups | Conc. of Prodigiosin (nM) | Viability (%) | | |
|---|---|---|---|---|
| | | 1st day | 2nd day | 3rd day |
| Non-treated | | 93 | 79 | 77 |
| Treated | 3 | 96 | 86 | 79 |
| | 10 | 89 | 82 | 79 |
| | 30 | 89 | 70 | 81 |
| | 100 | 82 | 70 | 70 |
| | 300 | 68 | 14 | 18 |
| | 1,000 | 74 | 14 | 14 |
| | 3,000 | 61 | 9 | 8 |
| | 10,000 | 32 | 4 | 4 |
| | 30,000 | 4 | 4 | 4 |

EXAMPLE III

In Vitro Experiment for the Effect of Prodigiosin on Immune Cell Proliferation Three standard substances which induce lymphocytes to proliferate were employed to measure the effect of the prodigiosin on proliferation of lymphocytes. 5 μg/ml of lipopolysaccharide were used to induce B lymphocyte to proliferate, 5 μg/ml of Concanavalin A for T lymphocyte and 5 μg/ml of Pokeweed mitogen for B and T lymphocytes, both. Prodigiosin was added, together with the proliferation-inducing substance. Three days after the addition, the proliferation effect was monitored by measuring the amount of DNA synthesized. In order to exclude the cytotoxicity of prodigiosin, it was used at a concentration of not more than 100 nM. The effect of prodigiosin on the proliferation of lymphocyte is shown in Table 2, below. In Table 2, the proliferation percentages mean the proliferated amounts of prodigiosin-treated lymphocytes relative to that of an non-treated group. As shown, the suppression percentage effected by prodigiosin in amounts of 30–100 nM reaches up to 96–98% for the T lymphocyte induced by concanavalin A while the proliferation of B lymphocyte induced by lipopolysaccharide and the proliferation of B/T lymphocytes induced by pokeweed mitogen are suppressed to the extent of 13–19% and 45–83%, respectively. Consequently, the data demonstrate that the prodigiosin of the present invention has a potential immunosuppressive activity which is exerted selectively on T lymphocytes.

TABLE 2

Effect of Prodigiosin on the Proliferation of Immune Cells

| Groups | Conc. of Prodigiosin (nM) | Proliferation (%) | | |
|---|---|---|---|---|
| | | B cell | T cell | B/T cells |
| Non-treated | | 100 | 100 | 100 |
| Treated | 3 | 101 | 77 | 100 |
| | 10 | 105 | 46 | 86 |
| | 30 | 87 | 4 | 55 |
| | 100 | 81 | 2 | 17 |

EXAMPLE IV

In Vitro Experiment for the Effect of Prodigiosin on the Immune Response

The influence of prodigiosin on the functions of lymphocytes was measured using three reaction systems. First, the ability of B lymphocyte to proliferate in response to lipopolysaccharide stimulus was assessed. For this, on the third day after stimulation with lipopolysaccharide, the antibody production of the B lymphocyte was measured. When B lymphocytes are stimulated with lipopolysaccharide, they can produce antibodies without the aid of T lymphocyte. Second, a mixed lymphocyte reaction was induced in order to assess the effect on T-cell response. The reaction needs no aids from the B lymphocyte. On the third day after two types of heteroimmune cells, which are different from each other in histocompatibility antigen, were mixed to stimulate the activity of T lymphocytes, the T-cell response-was assessed. Third, the T-cell dependent antibody producing reaction was utilized to assess the effect of prodigiosin on the simultaneous immune response of both of the B and T lymphocytes. This reaction requires the functions of B and T lymphocytes, simultaneously. On the fifth day after immunization of the lymphocytes with the red blood cells of sheep, their antibody production ability was assessed.

The effects of prodigiosin on the immune response of lymphocytes are shown in Table 3, below. As apparent from Table 3, the immune response in which T lymphocytes are involved is significantly suppressed whereas the B cell response is not at all throughout the concentration range. In Table 3, the values are relative to the immune response of the lymphocytes untreated with prodigiosin.

Taken together, the data of Examples III and IV demonstrate that the prodigiosin potentially suppresses the proliferation and immune response of T lymphocytes, selectively.

TABLE 3

Effect of Prodigiosin on the Immune Response of Immune Cells

| Groups | Conc. of Prodigiosin (nM) | Immune Response (%) | | |
|---|---|---|---|---|
| | | B cell | T cell | B/T cells |
| Non-treated | | 100 | 100 | 100 |
| Treated | 3 | 116 | 111 | 81 |
| | 10 | 108 | 110 | 74 |
| | 30 | 100 | 67 | 64 |
| | 100 | 97 | 30 | 34 |

EXAMPLE V

Selective Cytotoxicity of Prodigiosin for B, CD4 T and CD8 T Lymphocytes

Whether the selective immunosuppression of prodigiosin for T cells is attributed to the selective cytotoxicity for T cells or not was assayed by measuring the proportion of the cells. On the third day after treatment of the immune cells with prodigiosin, the number of the cells was counted. Because T lymphocytes consist of CD4 T cell (helper T cell) and CD8 T cell (cytotoxic T cell), the proportion of T and B lymphocytes was calculated in this Example. The results are shown in Table 4, below. The data of Table 4 show that the prodigiosin has no selective cytotoxicity. Thus, the selective immunosuppression for T lymphocytes is proved to be attributed to the suppression of immune response, but not of cytotoxicity. This result, together with the result of Example II, also demonstrates that the prodigiosin is not toxic within an effective experimental concentration range.

TABLE 4

Cytotoxicity of Prodigiosin on Lymphocytes

| Groups | Conc. of Prodigiosin (nM) | Proliferation (%) | | |
|---|---|---|---|---|
| | | B cell | CD4 T cell | CD8 T cell |
| Non-treated | | 47 | 31 | 12 |
| Treated | 3 | 47 | 31 | 13 |
| | 10 | 49 | 31 | 13 |

TABLE 4-continued

Cytotoxicity of Prodigiosin on Lymphocytes

| Groups | Conc. of Prodigiosin (nM) | Proliferation (%) | | |
|---|---|---|---|---|
| | | B cell | CD4 T cell | CD8 T cell |
| | 30 | 50 | 31 | 12 |
| | 100 | 52 | 29 | 10 |

EXAMPLE VI

In Vivo Experiment for the Effect of Prodigiosin on T Lymphocyte

A graft versus host reaction was utilized for the in vivo assay of prodigiosin's immunosuppression. The graft versus host reaction enables an assessment of the immune response of T lymphocytes. On the sixth day after transplantation of the T lymphocytes of BDF1 mice different in histocompatibility antigen, the lymphatic nodes were measured for weight, thereby assessing the immune response of T lymphocyte to the grafted heteroantigens. The prodigiosin was peritoneally injected at a dose of 30–100 mg per kg of body weight for five days while cyclophosphamide, as a positive control, was peritoneally injected at a dose of 100 mg/kg for five days. The body weights of the injected mice were measured to compare the toxicity of prodigiosin with that of cyclophosphamide. The results are given in Table 5, providing testimony that the prodigiosin potentially suppress the immune response of T lymphocytes, like the positive control, cyclophosphamide. As for the body weight, it was not changed in the mice injected with prodigiosin at an effective concentration. This demonstrates that the prodigiosin suppresses the immune response of T lymphocyte without exerting toxicity in vivo. In contrast, a loss of body weight occurred in the ice injected with cyclophosphamide at an effective concentration, showing the toxicity of the chemical.

TABLE 5

Effect of Prodigiosin on T Lymphocyte

| Groups | Conc. (mg/kg) | Wt. (mg) of Lymphatic node | Body weight (g) |
|---|---|---|---|
| Prodigiosin non-treated | | 3.54 | 22 |
| Prodigiosin Treated | 10 | 1.12 | 20 |
| | 30 | 0.98 | 21 |
| Positive Control (Cyclophosphamide) | 100 | 0.06 | 18 |

EXAMPLE VII

Effect of Prodigiosin on T Lymphocytes In Vivo (T-Cell Dependent Immune Response)

A T cell-dependent immune response reaction was used to assess the influence of prodigiosin on T lymphocytes in vivo. Test animals were immunized with sheep red blood cells by peritoneal injection. 4 days after the immunization, the number of the antibody producing cells was counted. Prodigiosin was peritoneally injected everyday. Based on the number of the antigen-producing cells in the non-treated animals, the influence of prodigiosin on T lymphocytes in vivo was assessed as percentage. Also, the weight ratio of the spleen to the body was measured to assay the toxicity of prodigiosin to the animals. Cyclophosphamide was used as a positive control.

The results are given in Table 6, below. As apparent from the data of Table 6, the number of the antibody-producing cells was significantly reduced by the treatment of prodigiosin, which is comparable to the positive control, cyclophosphamide, in the immunosuppression. Taking account of the weight ratio of the spleen to the body, the prodigiosin showed no toxicity at its effective concentrations while cyclophosphamide was very toxic at its effective concentration.

TABLE 6

Effect of Prodigiosin on T cell-Dependent Immune Response

| Groups | Conc. (mg/kg) | Immune Response (%) | Wt. Ratio of spleen/body (%) |
| --- | --- | --- | --- |
| Prodigiosin Treated | | 100 | 100 |
| Prodigiosin non-treated | 10 | 32 | 95 |
| | 30 | 27 | 84 |
| Positive Control (Cyclophosphamide) | 100 | 7 | 26 |

INDUSTRIAL APPLICABILITY

As apparent from the data of the Examples, the prodigiosin of the present invention has a potentially suppressive effect on the immune response of T lymphocytes, in vivo and in vitro, both. What is better, the prodigiosin shows no toxicity at its effective concentration ranges. Therefore, the prodigiosin of the present invention can be used as an immunosuppressive or a standard substance in various fields, including the treatment of the diseases requiring immunosuppression and the basic research for the diseases, the transplantation of organs or tissues, and the immune cells.

The invention claimed is:

1. A biologically pure culture of *Serratia marcescens* B-1231, KCTC 0386BP.

* * * * *